US009452250B2

(12) United States Patent
Penka et al.

(10) Patent No.: US 9,452,250 B2
(45) Date of Patent: Sep. 27, 2016

(54) DEVICE FOR PUMPING BLOOD IN AN EXTRACORPOREAL CIRCUIT

(75) Inventors: Ottmar Penka, München (DE); Johann Schreyer, München (DE); Erwin Knott, Poing (DE)

(73) Assignee: Sorin Group Deutschland GmbH, Munich (DE)

( * ) Notice: Subject to any disclaimer, the term of this patent is extended or adjusted under 35 U.S.C. 154(b) by 796 days.

(21) Appl. No.: 13/380,165

(22) PCT Filed: Apr. 23, 2010

(86) PCT No.: PCT/EP2010/055444
§ 371 (c)(1),
(2), (4) Date: Feb. 29, 2012

(87) PCT Pub. No.: WO2010/149408
PCT Pub. Date: Dec. 29, 2010

(65) Prior Publication Data
US 2012/0150089 A1    Jun. 14, 2012

(30) Foreign Application Priority Data
Jun. 25, 2009    (DE) .......... 10 2009 027 195

(51) Int. Cl.
*A61M 1/00* (2006.01)
*F04D 15/00* (2006.01)
(Continued)

(52) U.S. Cl.
CPC .......... *A61M 1/101* (2013.01); *A61M 1/1029* (2014.02); *A61M 1/1086* (2013.01); *A61M 1/122* (2014.02);
(Continued)

(58) Field of Classification Search
CPC .......... A61M 1/1086; A61M 1/3639; A61M 1/1613; A61M 1/1615; A61M 1/101; A61M 1/3663; A61M 2205/3331; A61M 2205/3334; A61M 2205/3341; A61M 2205/3351; A61M 2205/3355; A61M 2205/3365; A61M 2210/12; F04B 2201/1201; F04B 2203/0209; F04B 2203/1201; F04B 2203/1202; F04B 2205/01; F04B 2205/02; F04B 2205/05; F04B 2205/07; F04B 2205/09; F04D 27/001; F04D 27/004; F04D 27/00; F04D 15/00; F04D 15/0088; F04D 15/0094; F04D 15/0066
USPC .......... 604/4.01, 5.01, 6.11; 422/44
See application file for complete search history.

(56) References Cited

U.S. PATENT DOCUMENTS 3,551,072 A * 12/1970 Zimmerly .......... 417/45
3,588,589 A    6/1971 Emmasingel
(Continued)

FOREIGN PATENT DOCUMENTS

CN    86103696 A    1/1987
CN    1147964 A    4/1997
(Continued)

OTHER PUBLICATIONS

International Preliminary Report on Patentability issued in PCT/EP2010/055444, dated Oct. 5, 2011, 10 pages (with English translation).
(Continued)

*Primary Examiner* — Adam Marcetich
(74) *Attorney, Agent, or Firm* — Faegre Baker Daniels LLP

(57) ABSTRACT

A device for pumping blood in an extracorporeal circuit includes a centrifugal pump that suctions the blood to be pumped via a venous hose line connected to a suction side of the pump and releases it via an arterial hose line connected to a release side of the pump. The device includes a flow sensor that detects a released quantity on the release side of the pump and emits a measurement signal corresponding to the released quantity, a pressure sensor that detects the pressure on the release side of the pump and emits a measurement signal corresponding to the pressure, and an evaluation unit to which the measurement signals of the sensors are fed and which determines a value corresponding to the pressure on the suction side of the pump, taking into consideration the two measurements signals and the rotational speed of the centrifugal pump.

16 Claims, 1 Drawing Sheet

(51) Int. Cl.
*A61M 1/10* (2006.01)
*A61M 1/12* (2006.01)
*A61M 1/36* (2006.01)

(52) U.S. Cl.
CPC ......... *A61M 1/3639* (2013.01); *A61M 1/3663* (2013.01); *A61M 2205/3331* (2013.01); *A61M 2205/3351* (2013.01); *F04B 2205/02* (2013.01)

(56) References Cited

U.S. PATENT DOCUMENTS

| | | | |
|---|---|---|---|
| 3,851,181 A | 11/1974 | Heule | |
| 3,927,980 A | 12/1975 | Leonard | |
| 4,006,745 A | 2/1977 | Sorenson et al. | |
| 4,170,765 A | 10/1979 | Austin et al. | |
| 4,177,649 A * | 12/1979 | Venema | 62/209 |
| 4,193,004 A | 3/1980 | Lobdell et al. | |
| 4,309,871 A * | 1/1982 | Venema | F02C 9/28 417/43 |
| 4,466,804 A | 8/1984 | Hino | |
| 4,490,331 A | 12/1984 | Steg, Jr. | |
| 4,518,318 A * | 5/1985 | Jensen et al. | 417/53 |
| 4,599,093 A | 7/1986 | Steg, Jr. | |
| 4,642,089 A | 2/1987 | Zupkas et al. | |
| 4,664,682 A | 5/1987 | Monzen | |
| 4,678,404 A * | 7/1987 | Lorett et al. | 417/45 |
| 4,701,101 A | 10/1987 | Sapoff | |
| 4,705,497 A | 11/1987 | Shitaokoshi et al. | |
| 4,828,543 A | 5/1989 | Weiss et al. | |
| 4,846,800 A | 7/1989 | Ouriel et al. | |
| 4,876,066 A | 10/1989 | Bringham et al. | |
| 4,955,874 A | 9/1990 | Farrar et al. | |
| 4,984,462 A | 1/1991 | Hass, Jr. et al. | |
| 4,991,433 A | 2/1991 | Warnaka et al. | |
| 5,039,430 A | 8/1991 | Corey, Jr. | |
| 5,039,482 A | 8/1991 | Panzani et al. | |
| 5,043,707 A | 8/1991 | Heinze | |
| 5,049,146 A | 9/1991 | Bringham et al. | |
| 5,055,198 A | 10/1991 | Shettigar | |
| 5,061,236 A | 10/1991 | Sutherland et al. | |
| 5,078,677 A | 1/1992 | Gentelia et al. | |
| 5,110,549 A | 5/1992 | Gordon | |
| 5,112,480 A | 5/1992 | Hukasawa | |
| 5,147,187 A * | 9/1992 | Ito | A61M 1/101 415/900 |
| 5,158,533 A | 10/1992 | Strauss et al. | |
| 5,178,603 A | 1/1993 | Prince | |
| 5,186,431 A | 2/1993 | Tamarim | |
| 5,215,519 A | 6/1993 | Shettigar | |
| 5,226,265 A | 7/1993 | Kelly | |
| 5,240,380 A * | 8/1993 | Mabe | 417/43 |
| 5,270,005 A | 12/1993 | Raible | |
| 5,282,783 A | 2/1994 | Lindsay | |
| 5,303,585 A | 4/1994 | Lichte | |
| 5,304,164 A | 4/1994 | Lindsay | |
| 5,318,510 A | 6/1994 | Cathcart | |
| 5,399,074 A * | 3/1995 | Nose | A61M 1/101 415/900 |
| 5,403,273 A | 4/1995 | Lindsay | |
| 5,411,705 A | 5/1995 | Thor et al. | |
| 5,458,567 A | 10/1995 | Cathcart | |
| 5,458,579 A | 10/1995 | Chodorow et al. | |
| 5,563,490 A * | 10/1996 | Kawaguchi et al. | 318/808 |
| 5,586,085 A | 12/1996 | Lichte | |
| 5,619,993 A | 4/1997 | Lee | |
| 5,667,485 A | 9/1997 | Lindsay | |
| 5,725,357 A * | 3/1998 | Nakazeki et al. | 417/18 |
| 5,770,073 A | 6/1998 | Bach et al. | |
| 5,775,879 A * | 7/1998 | Durando | 417/45 |
| 5,800,721 A | 9/1998 | McBride | |
| 5,823,045 A | 10/1998 | Van Driel et al. | |
| 5,826,576 A | 10/1998 | West | |
| 5,849,186 A | 12/1998 | Raneri et al. | |
| 5,955,672 A | 9/1999 | Van Driel et al. | |
| 6,017,493 A | 1/2000 | Cambron et al. | |
| 6,048,363 A * | 4/2000 | Nagyszalanczy | A61M 1/101 415/900 |
| 6,287,270 B1 | 9/2001 | Fini | |
| 6,337,049 B1 | 1/2002 | Tamari | |
| 6,475,176 B2 | 11/2002 | Fini | |
| 6,564,627 B1 * | 5/2003 | Sabini et al. | 73/168 |
| 6,592,340 B1 * | 7/2003 | Horo et al. | 417/293 |
| 6,631,639 B1 | 10/2003 | Dam et al. | |
| 6,652,495 B1 | 11/2003 | Walker | |
| 6,694,570 B2 | 2/2004 | Chen | |
| 6,770,048 B2 | 8/2004 | Fini | |
| 7,072,769 B2 | 7/2006 | Fletcher-Haynes et al. | |
| 7,147,614 B2 | 12/2006 | Fini | |
| 7,591,812 B1 | 9/2009 | Tamari | |
| 7,694,570 B1 | 4/2010 | Dam et al. | |
| 8,500,673 B2 | 8/2013 | Zanotti et al. | |
| 8,506,513 B2 | 8/2013 | Rossi et al. | |
| 9,011,769 B2 | 4/2015 | Silvestri et al. | |
| 2001/0013822 A1 | 8/2001 | Nazarian et al. | |
| 2002/0032399 A1 | 3/2002 | Fini | |
| 2002/0033181 A1 * | 3/2002 | Groth et al. | 128/898 |
| 2002/0085952 A1 | 7/2002 | Ellingboe et al. | |
| 2002/0094300 A1 | 7/2002 | Yokoyama et al. | |
| 2003/0035730 A1 * | 2/2003 | Schob | 417/53 |
| 2003/0045772 A1 | 3/2003 | Riech et al. | |
| 2003/0139643 A1 * | 7/2003 | Smith | A61M 1/1031 600/16 |
| 2003/0144646 A1 | 7/2003 | Se et al. | |
| 2003/0175151 A1 | 9/2003 | Ghelli et al. | |
| 2004/0047737 A1 * | 3/2004 | Nose | A61M 1/101 417/44.1 |
| 2004/0064292 A1 * | 4/2004 | Beck et al. | 702/182 |
| 2004/0152944 A1 * | 8/2004 | Medvedev | A61M 1/101 600/17 |
| 2005/0025630 A1 * | 2/2005 | Ayre | A61M 1/101 417/53 |
| 2005/0119600 A1 * | 6/2005 | Lucke et al. | 604/6.15 |
| 2005/0230313 A1 | 10/2005 | O'Mahony et al. | |
| 2006/0015056 A1 | 1/2006 | Ellingboe et al. | |
| 2006/0089695 A1 | 4/2006 | Bolea et al. | |
| 2006/0150596 A1 | 7/2006 | Takahashi et al. | |
| 2006/0167400 A1 | 7/2006 | Ellingboe et al. | |
| 2006/0277269 A1 | 12/2006 | Dent et al. | |
| 2007/0017518 A1 * | 1/2007 | Farrugia et al. | 128/204.23 |
| 2007/0110612 A1 | 5/2007 | Ito | |
| 2007/0142923 A1 * | 6/2007 | Ayre et al. | 623/31 |
| 2007/0209662 A1 * | 9/2007 | Bowen et al. | 128/204.21 |
| 2008/0027368 A1 | 1/2008 | Kollar et al. | |
| 2008/0171960 A1 | 7/2008 | Brieske et al. | |
| 2008/0245530 A1 * | 10/2008 | Kuzmichev | 166/369 |
| 2008/0275377 A1 * | 11/2008 | Paolini et al. | 604/6.11 |
| 2009/0012443 A1 | 1/2009 | Ghelli et al. | |
| 2009/0099498 A1 | 4/2009 | Demers et al. | |
| 2009/0149950 A1 * | 6/2009 | Wampler | A61M 1/101 623/3.13 |
| 2010/0042038 A1 | 2/2010 | Urdahl et al. | |
| 2010/0140182 A1 | 6/2010 | Chapman et al. | |
| 2010/0275953 A1 * | 11/2010 | Orue Orue et al. | 134/18 |
| 2011/0098625 A1 * | 4/2011 | Masala et al. | 604/6.09 |
| 2011/0257576 A1 | 10/2011 | Simpson et al. | |
| 2011/0257578 A1 | 10/2011 | Zanotti et al. | |
| 2011/0257579 A1 | 10/2011 | Rossi et al. | |
| 2012/0130299 A1 | 5/2012 | Knott et al. | |
| 2013/0017119 A1 | 1/2013 | Silvestri et al. | |
| 2013/0303965 A1 | 11/2013 | Rossi et al. | |
| 2015/0196703 A1 | 7/2015 | Silvestri et al. | |

FOREIGN PATENT DOCUMENTS

| | | |
|---|---|---|
| CN | 1197677 A | 11/1998 |
| DE | 2455229 A1 | 5/1976 |
| DE | 2754894 A1 | 6/1979 |
| DE | 3935502 A1 | 5/1991 |
| DE | 19840399 A1 | 3/1999 |
| DE | 102004040441 | 6/2006 |
| DE | 102005001779 A1 | 9/2006 |
| DE | 102005029682 A1 | 12/2006 |
| DE | 102007026010 A1 | 12/2008 |
| EP | 0371173 A1 | 6/1990 |

(56) References Cited

FOREIGN PATENT DOCUMENTS

| | | |
|---|---|---|
| EP | 0472480 B1 | 2/1992 |
| EP | 0587251 B1 | 3/1994 |
| EP | 0820775 B1 | 1/1998 |
| EP | 0952433 A1 | 10/1999 |
| EP | 1053760 A2 | 11/2000 |
| EP | 1070509 A2 | 1/2001 |
| EP | 1210956 B1 | 6/2002 |
| EP | 2754458 A2 | 7/2014 |
| EP | 2435106 B1 | 11/2014 |
| EP | 2842584 A1 | 3/2015 |
| GB | 2009862 A | 6/1979 |
| GB | 2109934 A | 6/1983 |
| JP | 03091352 U | 9/1991 |
| JP | H03091352 U | 8/1994 |
| JP | 819602 A | 1/1996 |
| JP | 2944749 B2 | 6/1999 |
| JP | H11506701 A | 6/1999 |
| JP | 2000000299 A | 1/2000 |
| JP | 2001503665 A | 3/2001 |
| JP | 2001204815 A | 7/2001 |
| JP | 2001514939 A | 9/2001 |
| JP | 2001523339 A | 11/2001 |
| JP | 2002165878 A | 6/2002 |
| JP | 2003126246 A | 5/2003 |
| JP | 2005066013 A | 3/2005 |
| JP | 2006025531 A | 9/2006 |
| JP | 2006325750 A | 12/2006 |
| JP | 2007130290 A | 5/2007 |
| JP | 2008597 A | 1/2008 |
| JP | 2008194386 A | 8/2008 |
| JP | 2008270595 A | 11/2008 |
| JP | 2009240428 A | 10/2009 |
| JP | 2009287593 A | 12/2009 |
| JP | 2011076394 A | 4/2011 |
| WO | WO9421311 A2 | 9/1994 |
| WO | WO9624397 A2 | 8/1996 |
| WO | WO9733672 A1 | 9/1997 |
| WO | WO9820957 A1 | 5/1998 |
| WO | WO9848868 A1 | 11/1998 |
| WO | WO9908734 A1 | 2/1999 |
| WO | WO9965413 A1 | 12/1999 |
| WO | WO0015154 A1 | 3/2000 |
| WO | WO0044415 A1 | 8/2000 |
| WO | WO0147442 A1 | 7/2001 |
| WO | WO0176656 A2 | 10/2001 |
| WO | WO0239931 A1 | 5/2002 |
| WO | WO0239933 A1 | 5/2002 |
| WO | WO03026724 A1 | 4/2003 |
| WO | WO2006021295 A1 | 2/2006 |
| WO | WO2006057650 A2 | 7/2006 |
| WO | WO2008119993 A1 | 10/2008 |
| WO | 2010041604 A1 | 4/2010 |
| WO | WO02095675 A1 | 11/2012 |

OTHER PUBLICATIONS

International Search Report and Written Opinion issued in PCT/EP2010/055444, mailed Aug. 20, 2010, 10 pages (English Translation of SR).

Definition of "Cylinder", downloaded from http://dictionary.reference.com/browse/cylinder, download on Apr. 28, 2014, 3 pages.

European Search Report issued in EP 10160436, dated Nov. 5, 2010, 9 pages.

European Search Report issued in EP Application No. 03004815, completed Apr. 25, 2003, 3 pages.

European Search Report issued in EP Application No. 11162020, mailed Nov. 7, 2011, 8 pages.

European Search Report issued in EP Application No. 11173655, completed Nov. 30, 2011, 9 pages.

European Search Report issued in EP Application No. 12159592, mailed Apr. 24, 2012, 6 pages.

Extended European Search Report issued in 14188440.3, mailed Jan. 30, 2015, 7 pages.

Fischer, Gerhard, Betriebsmesstechnik, unveranderte Auflage, VEB Verlag Technik Berlin, 1986, 3 pages (machine translations: Business measuring technique, unchanged edition).

Henriksen Kenn et al., "Envisioning Patient Safety in the Year 2025: Eight Perspectives", Advances in Patient Safety: New Directions and Alternative Approaches, Agency for Healthcare Research and Quality. vol. 1, Aug. 2008.

International Preliminary Report on Patentability, Chapter II, issued in PCT/EP2010/055522, (with translation) mailed May 31, 2011, 13 pages.

International Search Report and Written Opinion issued in PCT/EP2010/055522, (with translation) mailed Aug. 6, 2010, 10 pages.

International Search Report and Written Opinion issued in PCT/IB2011/051639, mailed Nov. 18, 2011, 15 pages.

International Search Report issued in PCT/IB2012/053497, completed Nov. 15, 2012, 4 pages.

Klonoff, David C., "Designing an Artificial Pancreas System to be Compatible with Other Medical Devices", Journal of Diabetes Science and Technology, vol. 2, No. 5, Sep. 2008, pp. 741-745.

Terumo Europe Cardiovascular Systems, Innovative Products for the Treatment of Cardiovascular Disease, 2006 Terumo Europe, 105 pages.

van der Togt, Remko et al., "Electromagnetic Interference From Radio Frequency Identification Inducing Potentially Hazardous Incidents in Critical Care medical Equipment", JAMA, Jun. 25, 2008, vol. 299, No. 24, 7 pages.

Weber, Tim, "Talking Barcodes that Change our Lives", BBC News, published Apr. 48, 2004, 3 pages.

* cited by examiner

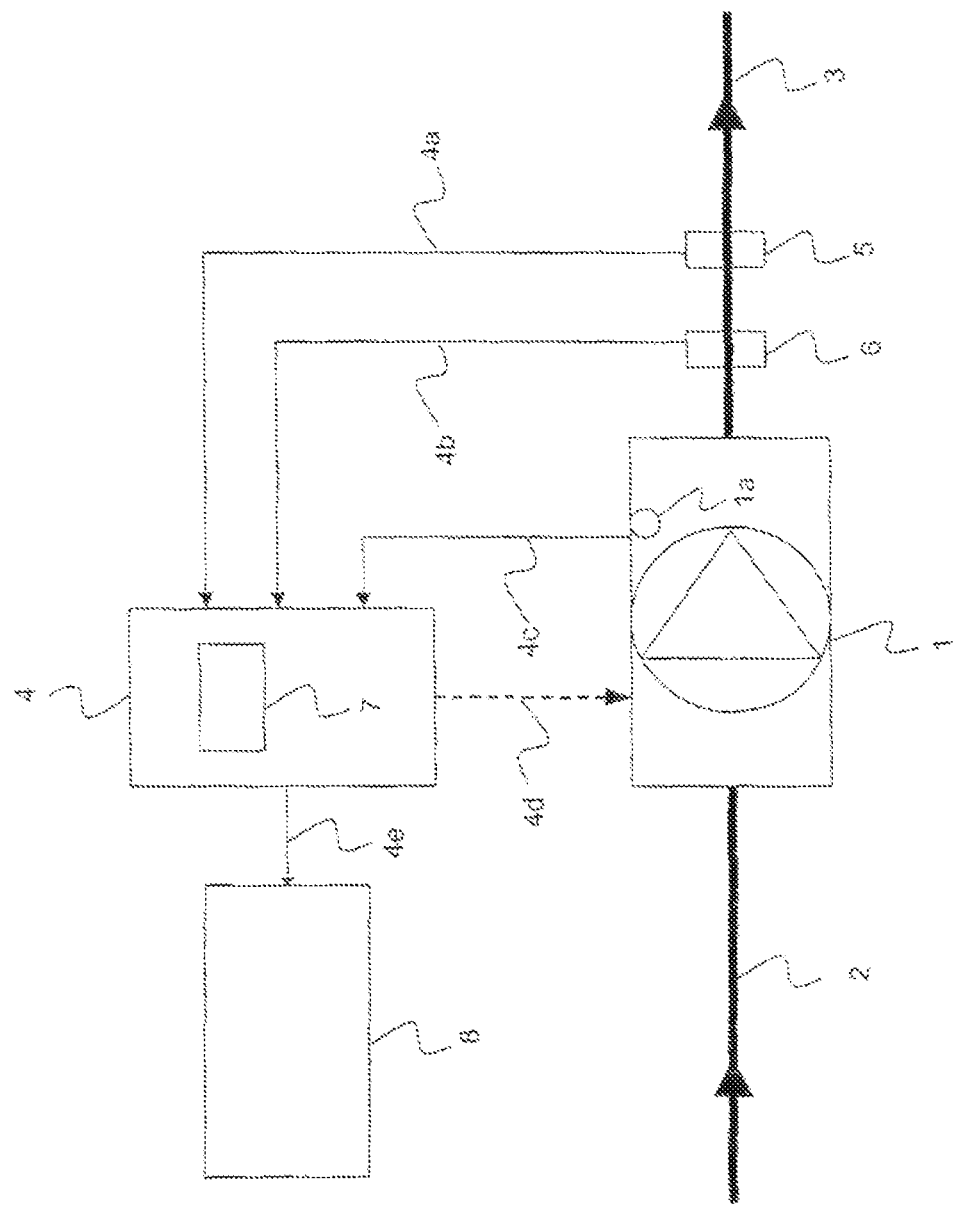

DEVICE FOR PUMPING BLOOD IN AN EXTRACORPOREAL CIRCUIT

CROSS-REFERENCE TO RELATED APPLICATION

The present application is a national phase application of PCT/EP2010/055444, filed pursuant to 35 U.S.C. §371, which claims priority to DE 10 2009 02 7195.3, filed Jun. 25, 2009. Both applications are incorporated herein by reference in their entirety.

TECHNICAL FIELD

The invention relates to a device for pumping blood in an extracorporeal circulation system including a centrifugal pump.

BACKGROUND

Pumping blood in an extracorporeal blood circulation system comprising a centrifugal pump is known, for example, from DE 39 35 502 A1. In these devices, a venous hose line conveys the blood from the patient to the pump and an arterial hose line conveys the blood away from the pump. Since, in these devices, the centrifugal pump is directly connected to the venous inflow line, an excessively high vacuum may occur in the venous hose line if the suction power of the pump is too high, which leads to the blood being damaged. In order to prevent this, the vacuum can be detected on the suction side of the pump by means of a sensor so as to initiate suitable countermeasures against an excessively high vacuum upon reaching a predetermined value, for example by alerting an operator or automatically intervening in the pump operation.

However, detecting the vacuum on the venous side of the pump is problematic since owing to the vacuum prevailing here (as compared to the atmospheric pressure), air could penetrate into the blood circulation system if leaks occur at the site of the pressure sensor. Detecting air penetrating the system as a result of this problem is not practicable; at the same time, air which enters the extracorporeal blood circulation system represents a significant danger to the patient.

Against this background, the problem forming the basis for the invention is to specify a manner in which a reliable value corresponding to the amount of vacuum on the suction side of the pump can be obtained without using a pressure sensor on the venous side of the pump for this purpose.

SUMMARY

In some embodiments, this problem is solved via a device for pumping blood in an extracorporeal circulation system, including a centrifugal pump that sucks in the blood to be pumped via a venous hose line connected to the suction side of the pump and discharges the blood via an arterial hose line connected to the discharge side of the pump. The device includes a flow sensor which detects the discharged quantity on the discharge side of the pump and outputs a measurement signal corresponding to the discharged quantity, a pressure sensor which detects the pressure on the discharge side of the pump and outputs a measurement signal corresponding to the pressure, and an evaluation unit to which the measurement signal of the flow sensor and the measurement signal of the pressure sensor are supplied and which determines a value corresponding to the pressure on the suction side of the pump, taking into consideration the two measurement signals and the rotational speed of the centrifugal pump.

In an advantageous embodiment, the evaluation unit uses a set of characteristics of the centrifugal pump when determining the value corresponding to the pressure on the suction side of the pump.

In a further advantageous embodiment, the set of characteristics of the centrifugal pump is stored in a memory in the evaluation unit.

In a further advantageous embodiment, the evaluation unit is connected to a display means for displaying at least the vacuum on the suction side of the pump and/or for alerting an operator.

In a further advantageous embodiment, a measurement signal from a rotational speed sensor is supplied to the evaluation unit.

In a further advantageous embodiment, a control signal from the pump, which determines or represents the rotational speed of the pump, is supplied to the evaluation unit.

In a further advantageous embodiment, the evaluation unit assumes the function of a control device for the centrifugal pump or is integrated in a control device for the centrifugal pump such that a control signal determining the rotational speed of the centrifugal pump can be supplied to the centrifugal pump.

In a further advantageous embodiment, the evaluation unit reduces the rotational speed of the pump upon reaching a predetermined value for the pressure on the suction side of the pump.

BRIEF DESCRIPTION OF THE FIGURES

An embodiment of the invention will be described in more detail in the following with reference to the drawing.

FIG. 1 shows the structure of an embodiment of a device according to the invention.

DETAILED DESCRIPTION

The embodiment of a device according to the invention for pumping blood in an extracorporeal circulation system, as shown in FIG. 1, includes a centrifugal pump 1 that sucks in the blood to be pumped via a venous hose line 2 connected to the suction side of the pump. The venous hose line 2 may be directly connected to a patient whose blood is being pumped in the extracorporeal blood circulation system. However, other components of the circulation system which are not shown in FIG. 1 may additionally be integrated in the venous line. The centrifugal pump 1 discharges the blood to the arterial section of the extracorporeal blood circulation system via an arterial hose line 3 connected to the discharge side of the pump.

A flow sensor 5 and a pressure sensor 6 are provided on the arterial side of the pump. The flow sensor 5 is used to detect the discharged quantity on the discharge side of the pump 1 and outputs a measurement signal corresponding to the discharged quantity. The pressure sensor 6 is used to detect the pressure on the discharge side of the pump 1 and outputs a measurement signal corresponding to the flow rate. It must be noted with regard to the pressure sensor 6 that this measuring site is not critical since a positive pressure (as compared to the atmospheric pressure) prevails on the arterial side of the pump, and thus if a leak should occur in the region of the measuring site, the penetration of air into the arterial hose line 3 would not occur, rather at most blood may escape out of the arterial hose line 3.

As FIG. 1 furthermore shows, the embodiment of a device according to the invention as described herein also includes an evaluation unit 4 to which the measurement signal of the flow sensor 5 and the measurement signal of the pressure sensor 6 are supplied. A further signal is also supplied to the evaluation unit, for example the measurement value of a rotational speed sensor 1a or the control signal of the pump which corresponds to the rotational speed of the centrifugal pump 1. As FIG. 1 shows, the measurement signals and the further signal are supplied to the evaluation unit 4 via signal lines 4a to 4c in the embodiment described herein. If the evaluation unit 4 is integrated in a control device for controlling the pump, the separate supply of a rotational-speed-dependent signal is not necessary. In FIG. 1, this configuration is indicated in that a (dashed) control signal line 4d is provided, via which the evaluation unit 4, configured in this case as a control device, supplies a control signal to the pump 1 and in this manner directly determines the rotational speed of the pump.

The evaluation unit 4 in any case evaluates the measurement signals and the rotational speed of the centrifugal pump and, on the basis of the measurement signals and the rotational speed, determines a value which corresponds to the pressure on the suction side of the pump. Advantage is thereby taken of the fact that the pressure increase (gradient outlet pressure-inlet pressure) via a centrifugal pump is a function of the rotational speed and the flow, which can be described, for example, with the aid of a set of characteristics. Changes to resistances on the venous or arterial side of the pump do not have any influence thereon. Thus, if the pressure on the discharge side is known and the flow and rotational speed are also known, the pressure on the suction side can be determined by first of all determining the pressure increase via the pump using the set of characteristics (and possible interpolation between support values of the set of characteristics) and then subtracting the pressure increase determined in this manner from the pressure on the discharge side of the pump.

In some embodiments, the set of characteristics must be determined in advance for a specific type of centrifugal pump by means of measurement technology. The values of the set of characteristics may be stored in a memory 7 in the evaluation unit 4 such that when determining the value corresponding to the pressure on the suction side of the pump, the evaluation unit can access the set of characteristics of the centrifugal pump, whereby the measurement signals of the sensors on the arterial side and the rotational speed can be used as access parameters. If a support value for a given parameter combination is not provided in the set of characteristics, a suitable point in the set of characteristics is determined by means of (linear) interpolation.

If the evaluation unit 4 detects an excessive vacuum on the venous side of the centrifugal pump, an alarm indicator can be output to the operator via a display means 8. The operator will then take suitable countermeasures to reduce the vacuum in the venous line. For this purpose, the evaluation unit 4 is connected to the display means 8 via a signal line 4e. With the aid of the display means 8, it is furthermore possible for the evaluation unit 4 to provide a continuous pressure display at least for the vacuum on the venous side of the pump so that the operator has an overview of the current pressure conditions during operation.

If, as described above, the evaluation unit 4 also assumes the function of a control device or is integrated in a control device, it is possible in the case of an excessive vacuum on the venous side of the centrifugal pump to directly intervene in the operation of the pump and to reduce the rotational speed in order to lower the vacuum in the venous line. The already addressed control signal line 4d may be used to supply a corresponding control signal to the pump 1.

The invention claimed is:

1. A device for pumping blood in an extracorporeal circulation system, the device comprising:
    a centrifugal pump having a suction side and a discharge side, the pump configured to receive blood from a venous hose line connected to the suction side and to discharge blood via an arterial hose line connected to the discharge side;
    a flow sensor configured to detect a discharged quantity on the discharge side of the pump and output a flow measurement signal corresponding to the discharged quantity;
    a discharge side pressure sensor configured to detect discharge side pressure of the pump and output a discharge side pressure measurement signal corresponding to the discharge side pressure;
    a rotational speed sensor configured to detect a rotational speed of the centrifugal pump and output a rotational speed signal corresponding to the rotational speed of the centrifugal pump; and
    an evaluation unit to which the flow measurement signal of the flow sensor, the discharge side pressure measurement signal, and the rotational speed signal of the rotational speed sensor are supplied, the evaluation unit configured to calculate a suction side pressure value corresponding to a suction side pressure of the pump based on the flow measurement signal from the flow sensor, the discharge side pressure measurement signal from the pressure sensor on the discharge side of the pump and the rotational speed signal from the rotational speed sensor, wherein the evaluation unit generates a control signal for controlling the rotational speed of the centrifugal pump, based on the suction side pressure value.

2. A device according to claim 1, wherein the evaluation unit accesses values of a set of characteristics of the centrifugal pump when determining the suction side pressure value corresponding to the suction side pressure, said set of characteristics being determined in advance for said centrifugal pump.

3. A device according to claim 2, wherein the values of the set of characteristics of the centrifugal pump are stored in a memory in the evaluation unit.

4. A device according to claim 1, further comprising a display means, the evaluation unit being connected to the display means for displaying at least the suction side pressure value of the suction side pressure and/or for alerting an operator.

5. A device according to claim 1, wherein the evaluation unit functions as a control device for the centrifugal pump.

6. A device according to claim 5, wherein the evaluation unit reduces the rotational speed of the pump when a predetermined value for the suction side pressure is reached.

7. A device according to claim 5, wherein the evaluation unit reduces the rotational speed of the pump when the evaluation unit calculates the suction side pressure to be indicative of an excessive vacuum.

8. A device according to claim 1, wherein the evaluation unit is integrated into a control device for the centrifugal pump such that the control signal for controlling the rotational speed of the centrifugal pump can be supplied to the centrifugal pump.

9. A device for pumping blood in an extracorporeal circulation system, the device comprising:
- a centrifugal pump having a suction side and a discharge side, the pump configured to receive blood from a venous hose line connected to the suction side and to discharge blood via an arterial hose line connected to the discharge side;
- a flow sensor configured to detect a discharged quantity on the discharge side of the pump and output a flow measurement signal corresponding to the discharged quantity;
- a discharge side pressure sensor configured to detect discharge side pressure of the pump and output a discharge side pressure measurement signal corresponding to the discharge side pressure;
- a rotational speed sensor configured to detect a rotational speed of the centrifugal pump and output a rotational speed signal corresponding to the rotational speed of the centrifugal pump; and
- an evaluation unit to which the flow measurement signal of the flow sensor, the discharge side pressure measurement signal, and the rotational speed signal of the rotational speed sensor are supplied, the evaluation unit configured to calculate a suction side pressure value corresponding to a suction side pressure of the pump based on the flow measurement signal from the flow sensor, the discharge side pressure measurement signal from the pressure sensor on the discharge side of the pump, and the rotational speed signal from the rotational speed sensor,
- wherein the evaluation unit functions as a control device for the centrifugal pump and accesses values of a set of characteristics of the centrifugal pump when determining the suction side pressure value corresponding to the suction side pressure on the suction side of the pump, said set of characteristics being determined in advance for said centrifugal pump, and the evaluation unit reduces the rotational speed of the centrifugal pump upon reaching a predetermined value for the suction side pressure.

10. A device according to claim 9, wherein the values of the set of characteristics of the centrifugal pump are stored in a memory in the evaluation unit.

11. A device according to claim 9, further comprising a display means, the evaluation unit being connected to the display means for displaying at least the suction side pressure value of the suction side pressure and/or for alerting an operator.

12. A device according to claim 9, wherein the evaluation unit is integrated into a control device for the centrifugal pump such that a control signal determining the rotational speed of the centrifugal pump can be supplied to the centrifugal pump.

13. A device for pumping blood in an extracorporeal circulation system, the device comprising:
- a centrifugal pump having a suction side and a discharge side, the pump configured to receive blood from a venous hose line connected to the suction side and to discharge blood via an arterial hose line connected to the discharge side;
- a flow sensor configured to detect a discharged quantity on the discharge side of the pump and output a flow measurement signal corresponding to the discharged quantity;
- a discharge side pressure sensor configured to detect discharge side pressure of the pump and output a discharge side pressure measurement signal corresponding to the discharge side pressure;
- a rotational speed sensor configured to detect a rotational speed of the centrifugal pump and output a rotational speed signal corresponding to the rotational speed of the centrifugal pump;
- an evaluation unit to which the flow measurement signal of the flow sensor, the discharge side pressure measurement signal, and the rotational speed signal of the rotational speed sensor are supplied, the evaluation unit configured to calculate a suction side pressure value corresponding to a suction side pressure of the pump based on the flow measurement signal from the flow sensor, the discharge side pressure measurement signal from the pressure sensor on the discharge side of the pump, and the rotational speed signal from the rotational speed sensor, wherein the evaluation unit generates a control signal for controlling the rotational speed of the centrifugal pump, based on the suction side pressure value, and supplies the control signal to the evaluation unit; and
- a display means, the evaluation unit being connected to the display means for displaying at least the suction side pressure value of the suction side pressure and/or for alerting an operator.

14. A device according to claim 13, wherein the evaluation unit accesses values of a set of characteristics of the centrifugal pump when determining the suction side pressure value corresponding to the suction side pressure, said set of characteristics being determined in advance for said centrifugal pump.

15. A device according to claim 14, wherein the values of the set of characteristics of the centrifugal pump are stored in a memory in the evaluation unit.

16. A device according to claim 13, wherein the evaluation unit is integrated into a control device for the centrifugal pump such that the control signal determining the rotational speed of the centrifugal pump can be supplied to the centrifugal pump.

* * * * *